US005756482A

United States Patent [19]
Roberts et al.

[11] Patent Number: 5,756,482
[45] Date of Patent: *May 26, 1998

[54] METHOD OF ATTENUATION OF NERVOUS SYSTEM DAMAGE

[75] Inventors: Eugene Roberts, Monrovia, Calif.; Lloyd Guth, Ford's Colony, Va.

[73] Assignee: The Center for Innovative Technology, Herndon, Va.

[*] Notice: The term of this patent shall not extend beyond the expiration date of Pat. No. 5,574,022.

[21] Appl. No.: 648,914

[22] Filed: May 16, 1996

Related U.S. Application Data

[63] Continuation of Ser. No. 227,533, Apr. 14, 1994, Pat. No. 5,574,022.

[51] Int. Cl.$^6$ .................. A61K 31/715; A61K 31/60; A61K 31/56
[52] U.S. Cl. .................. 514/54; 514/165; 514/169; 514/171; 514/177; 514/178; 514/182; 514/885
[58] Field of Search .................. 514/54, 165, 169, 514/171, 177, 178, 182, 885; 536/123.1

[56] References Cited

U.S. PATENT DOCUMENTS

| | | | |
|---|---|---|---|
| 4,560,557 | 12/1985 | Wilson et al. | 514/178 |
| 4,996,318 | 2/1991 | Gall et al. | 544/295 |
| 5,202,126 | 4/1993 | Perrier et al. | 424/450 |
| 5,212,167 | 5/1993 | Farb | 514/178 |
| 5,366,968 | 11/1994 | Farb | 514/178 |
| 5,574,022 | 11/1996 | Roberts et al. | 514/54 |

OTHER PUBLICATIONS

John F. Kennedy, Carbohydrate Chemistry, 6.4 Microbial polysaccharides pp. 250–255, 1988.

Fong–Sen Wu, et al., Pregnenolone Sulfate: A Positive Allosteric Modulator At The N–Methyl–D–Aspartate Receptor, Molecular Pharmacology, 40:333–336, 1991.

Michael B. Bracken, Ph.D., et al., A Randomized Controlled Trial of Methyl–Prednoisolone or Naloxone In The Treatment of Active Spinal–Cord Injury, The New England Journal of Medicine, vol. 322, No. 20, pp. 1405–1412, May 1990.

William G. Lavelle, M.D., Treatment of Spinal–Cord Injury, The New England Journal of Medicine, vol. 322, No. 20, pp. 1459–1461, May 17, 1990.

Alan L. Faden, M.D., et al., Comparison of Thyrotropin–Releasing Hormone (TRH) naloxone, and Dexamethasone Treatments in Experimental Spinal Injury, Neurology, vol. 33, No. 6, pp. 673–678, Jun. 1983.

Motonobu Satoh, et al., Role of In–Vivo Scavenger Function of Macrophages In Priming For Endogenous Production Of Tumor Necrosis Factor, Journal of Biological Response Modifiers, vol. 6, pp. 499–511, Feb. 1987.

Tarlov Scores: Rats Treated With Preg+LPS+Naproxen Or Vehicle, Sep. 3, 1995.

ME Snider, et al., Production Of Arachidonic Acid Metabolites By Operationally Defined Macrophage Subsets, Prostaglandins 25:491–501, 1983.

MJ Pabst, et al., Human Macrophages May Normally Be "Primed" For A Strong Oxygen Radical Response, Adv. Exp. Med. Biol. 166: 215–221, 1983.

GW Duff, et al., The Pyrogenic And Mitogenic Actions Of Interleukin–1 Are Related, Nature 30: 449–451, 1983.

AE Koch, et al., Induction of Neovascularization By Activated Human Monocytes, J. Leukocyte Biol. 39:233–238, 1986.

Giulian, et al., Interleukin–1 Stimulation Of Astroglial Proliferation After Brain Injury, Science, 228:497–499, 1985.

Logan, et al., Enhanced Expression Of Transforming Growth Factor Beta 1 In The Rat Brain After A Localized Cerebral Injury., Brain Res. 587:216–225, 1992.

Lee, et al., Cytokine Production By Human Fetal Microglia And Astrocytes, Differential Induction By LPS And IL–1 Beta., J. Immunol. 150:2659–2667, 1993.

Lieberman, et al., Production Of Tumor Necrosis Factor And Other Cytokines By Astrocytes Stimulated With Lipopolysaccharide Or A Neurotropic Virus., Proc. Nat. Acad. Sci 86:6348–6352, 1989.

Shari, et al., Human Astrocyte Production Of Tumor Necrosis Factor–Alpha, Interleukin–1 Beta, And Interleukin–6 Following Exposure To Lipopolysaccharide Endotoxin, Neurol. Res., 15:109–112, 1993.

Roberts, E., Living Systems Are Tonically Inhibited, Autonomous Optimizers, And Disinhibition Coupled to Variability Generation Is Their Major Organizing Principle: Inhibitory Command–Control At Levels Of Membrane, Genome, Metabolism, Brain, And Society., Neurochem Res., 16:409–421, 1991.

Roberts, E., Dehydroepiandrosterone (DHEA) And Its Sulfate (DHEAS) As Neural Facilitators: Effects On Brain Tissue In Culture And On Memory In Young And Old Mice. A Cyclic GMP Hypothesis Of Action Of DHEA In Nervous System And Other Tissues. In: The Biological Role of Dehydropeiandrosterone (DHEA) (Eds. Kalimi M and Regelson W), pp. 13–40, Walter de Gruyter & Co., Berlin, 1990.

Flood, et al., Memory–Enhancing Effects In Male Mice Of Pregnenolone And Steroids metabolically Derived From It, Proc. Natl. Acad. Scie USA 89:1567–1571, 1992.

Jensen, EV., Steroid Hormone Receptors, Curr Top Pathol., 83:365–431, 1991.

Carson–Jurica, MA., et al., Steroid Receptor Family: Structure And Functions, Endocr Rev. 11:201–220, 1990.

Wahli, W et al., Superfamily Of Steroid Nuclear Receptors: Positive And Negative Regulators Of Gene Expression. FASEB J 5:2243–2249, 1991.

(List continued on next page.)

*Primary Examiner*—John Kight
*Assistant Examiner*—Howard C. Lee
*Attorney, Agent, or Firm*—Whitham, Curtis, Whitham & McGinn

[57] ABSTRACT

A method is disclosed for attenuation of nervous system damage after injury which comprises administering therapeutic amounts of PREG, PREG–S, or esters of PREG or PREG–S together with an enhancer of secretory processes in non-neural cells such as a bacterial lipopolysaccharide and a non-steroidal antiinflammatory substance such as indomethacin.

8 Claims, 4 Drawing Sheets

OTHER PUBLICATIONS

Beato, M. et al., Transcriptional Control By Nuclear Receptors. FASEB J 5:2044–2051, 1991.

Moore, DD et al., Promiscuous Behaviour In The Steroid Hormone Receptor Superfamily. Tins 12:165–168, 1989.

Evans, RM. The Steroid And Thyroid Hormone Receptor Superfamily. Science 240: 889–895, 1988.

Schwabe, J. et al., Beyond Zinc Fingers: Steroid Hormone Receptors Have A Novel Structural Motif For DNA Recognition. TIBS. 16:291–296, 1991.

Burstein, S et al., Biosynthesis Of Pregnenolone. Recent Prog. Horm Res. 27:303–249, 1971.

Prasad, VVK. et al., Reconsidering Some Of The Biosynthetic Pathways Leading To Formation Of $C_{19}$–Steroids.Ann NY Acad. Sci. 595:1–16, 1990.

Lieberman, S et al., A Heuristic Proposal For Understanding Steroidogenic Processes. Endocr Rev. 5:128–148, 1984.

Leszczynski, DE et al., Metabolic Conversion Of Six Steroid Hormones By Human Plasma High–Density Lipoprotein. Biochem Biophys Acta 1083:18–28, 1991.

Provencher, PH et al., Pregnenolone Fatty Acid Esters Incorporated Into Lipoproteins: Substrates In Adrenal Steroidogenesis. Endocrinology 130:2717–2724, 1992.

Mather, et al., Steroids And Their Conjugates In The Mammalian Brain. Proc. Natl. Acad Sci USA 90:85–88, 1993.

Castagnetta, L et al., Steroid Formation, Degradation, And Action In Peripheral Tissues. Ann Ny Acad. Sci 595:1–489, 1990.

Frairia, R et al., Protein Interactions: Basic And Clinical Aspects. Ann NY Acad. Sci. 538:1–326, 1988.

Majewska, et al., Neurosteroids: Endogenous Bimodal Modulators Of The $GABA_A$ Receptor. Mechanism of Action And Physiological Significance. Progr.Neurobiol 38:379–395, 1992.

Meinville,J–M et al., Pregnenolone Sulfate Antagonizes $GABA_A$ Receptor–Mediated Currents Via A Reduction Of Channel Opening Frequency. Brain Res 489:190–194, 1989.

Woodward, RM et al., Effects Of Steroids On $\gamma$–Aminobutyric Acid Receptors Expressed In Xenopus Oocytes By Poly (A)* RNA From Mammalian Brain And Retina. Mol Pharm 41;89–103, 1992.

Bowlby, MR et al., Pregnenolone Sulfate Potentiation Of N–Methyl–D–Aspartate Receptor Channels In Hippocampal Neurons. Mol Pharm 43:813–819, 1993.

Farb, DH et al., Steroid Modulcation Of Amino Acid Neurotransmitter Receptors. Adv. Biochem Psychopharmacol. 47:119–131, 1992.

Irwin, RP et al., Pregnenolone Sulfate Augments NMDA Receptor Mediated Increases In Intracellular $CA^{2+}$ In Cultured Rat Hoppocampal Neurons.Neurosci. Lett 141:30–34, 1992.

Roberts, E et al., Serum Steroid Levels In Two Old Men With Alzheimer's Disease (AD) Before, During, And After Oral Administration Of Dehydroepiandrosterone DHEA. Pregnenolone Synthesis May Become Rate–Limiting In Aging. In: The Biological Role of Dehydroepiandrosterone (DHEA) Eds., Kalimi M and Regelson W pp.43–63. Walter de Gruyter & Co., Berlin, 1990.

Lanthier A et al., Sex Steroids And 5–EN–3β–Hydroxysteroids In Specific Regions Of The Human Brain And Cranial Nerves. J Steroid Biochem 25:445–449, 1986.

Morfin R et al., Neurosteroids: Pregnenolone In Human Sciatic Nerves., Proc Natl. Acad. Sci. USA 89:6790–6793, 1992.

Le Goascogne C et al., Neurosteroids: Cytochrome P–$45_{sec}$ In Rat Brain. Science 237:1212–1215, 1987.

Hu ZY et al., Neurosteroids: Oligodendrocyte Mitochondria Convert Cholesterol To Pregnenolone. Proc Natl Acad Sci USA 84:8215–8219, 1987.

Jung–Testas I et al., Steroid Synthesis In Rat Brain Cell Cultures. J. Steroid Biochem 34:511–519, 1989.

Jung–Testas I et al., Neurosteroids: Biosynthesis Of Pregnenolone And Progesterone In Primary Cultures Of Rat Glial Cells. Endocrinology 125:2083–2091, 1989.

Akwa, Y. et al., Neurosteroids: Biosynthesis, Metabolism And Function Of Pregnenolone And Dehydroepiandrosterone In The Brain. J. Steroid Biochem. Molec. Biol. 40:71–81, 1991.

Vourc'h C, et al., $\Delta^5$–3β–Hydroxysteroid Acyl Transferase Activity In The Rat Brain. Steroids 57:210–215, 1992.

Roberts, E et al., Pregnenolone—From Selye To Alzheimer And A Model Of The Pregnenolone Binding Site On The $GABA_A$ Recept. Biochem. Pharm. In press, 1994.

Henderson, E et al., Pregnenolone, J Clin Endocrin 10:455–474, 1950.

Hoagland H., Adventures In Biological Engineering. Science 100:63–67, 1944.

Pincus, G et al., Effects Of Administered Pregnenolone On Fatiguing Psychomotor Performance. J Aviat Med 15:98–115, 1944.

Pincus G et al., Effects On Industrial Production Of The Administration Of Δ5 Pregnenolone To Factory Workers, I. Psychosom Med 7:342–346, 1945.

Pincus G et al., Effects On Industrial Production Of The Administration Of Δ5 Pregnenolone To Factory Workers, II. Psychosom Med 7:347–352, 1945.

Ishmael Wk. et al., The Effects Of Certain Steroid Compounds On Various Manifestations Of Rheumatoid Arthritis. J Okla State Med Assoc., 42:434–437, 1949.

Freeman, H et al., Therapeutic Efficacy Of Δ5 Pregnenolone In Rheumatoid Arthritis. Jama 142:1124–1128, 1950.

Freeman, H et al., Oral Steroid Medication In Rheumatoid Arthritis. J. Clin Endocrin 10:1523–1532, 1950.

Freeman, H et al., Oral Steroid Medication In Rheumatoid Arthritis. In: Symposium on Steroids in Experimental and Clinical Practice (Ed. White A), pp. 181–198, Blakiston, NY, 1951.

Davison, R et al. Effects Of Delta 5 Pregnenolone In Rheumatoid Arthritis. Arch. Intern Med 85:365–388, 1950.

McGavack TH, et al., The Use Of Δ5–Pregnenolone In Various Clinical Disorders. J. Clin Endocrinol 11: 559–577, 1951.

Steiger, A et al., Neurosteroid Pregnenolone Induces Sleep–EEG Changes In Man Compatible With Inverse Agonistic $GABA_A$–Receptor Modulation. Brain Res 615:267–274, 1993.

Wrathall, JR, et al., Spinal Cord Contusion In The Rat: Production Of Graded, Reproducible Injury Groups. Exp Neurol 88:108–122, 1985.

Abelson and Tukey, Efficient Conversion Of Nonparametric Information Into A Metric System, Quantitative Analysis of Social Problems (E.R. Rufte, ed.) Addison–Wesley, Reading, MA, 1967.

Bahr, G.M., et al., Induction, In Vitro And In Vitro, Of Macrophage Membrane Interleukin–1 By Adjuvant Active Synthetic Muramyl Peptides., Cell. Immunol. 107:443–454, 1987.

Bodgan, C., et al., Modulation Of Macrophage Function By Transforming Growth Factor BETW, Interleukin–4, And Interleukin–10. Ann. NY Acad Sci., 685:713–739, 1993.

Cummings, NP, et al., Oxidative Metabolic Response And Microbicidal Activity Of Human Milk Macrophages: Effect Of LPS And Muramyl Dipeptide. Infect. & Immun. 49:435–439, 1985.

Endo, Y. Induction Of Histidine Decarboxylase In Mouse Tissues By Mitogens In Vivo. Biochem. Pharmacol. 32:3835–3838, 1983.

Guth, L. et al., Spinal Cord Injury In The Rat: Treatment With Bacterial Lipo–Polysaccharide And Indomethacin Enhances Cellular Repair And Locomotor Function Exp. Neurol. 126:76–87, 1994.

Hunt, TK, et al., Studies On Inflammation And Wound Healing: Angiogensis And Collagen Synthesis Stimulated In Vivo By Resident And Activated Wound Macrophages. Surgery 96:48–54, 1984.

Johnson, W.J., et al., Rat Macrophage Treatment With Lipopolysaccharide Leads To A Reduction In Respiratory Burst Product Secretion And A Decrease In NADPH Oxidase Affinity. Cell. Immunol. 108:109–119, 1987.

Karnovsky, ML. Muramyl Peptides In Mammalian Tissues And Their Effects At The Cellular Level. Fed. Proc. 45:2556–2560, 1986.

Koestler, T.P., et al., Induction By Immunomodulatory Agents Of A Macrophage Antigen Recognized By Monoclonal Antibody 158.2 And Correlation With Macrophage Function. Cell. Immunol. 96:113–125, 1985.

Mehta, K., et al., Stimulation Of Macrophage Protease Secretion via Liposomal Delivery Of Muramyl Dipeptide Derivatives To Intracellular Sites. Immunology. 51:517–527, 1984.

Pabst, MJ, et al., Inhibition Of Macrophage Priming By Sulfatide From Myco–Bacterium Tuberculosis. J. Immunol. 140:634–640, 1988.

Peterson, TC, et al., The Role, Of Lymphocytes, Macrophages And Interferon In The Depression Of Drug Metabolism By Dextran Sulfate. Immunopharmacol. 11:21–28, 1986.

Riveau, G., et al., Disociation Between Muramyl Dipeptide–Induced Fever And Changes In Plasma Metal levels., Am J. Physiol. 250:C572–C577, 1986.

St. Georgieve, V., et al., "Immunomodulating Drugs", The New York Academy of Sciences: NY 816 Pages, 1993.

Speer, CP., et al., Enhanced Release Of Oxygen Metabolites By Monocyte–Derived macrophags Exposed To Proteolytic Enzymes; Activity Of Neutrophil Elastase And Cathepsin, G. J. Immunol. 133:2151–2156, 1984.

Strassman, G., et al., Antigens Associated With The Activation Of Murine Mononuclear Phagocytes In Vivo: differential Expression Of Lymphocyte Function–Associated Antigen In The Several Stages Of Development. Cell. Immunol. 94:265–275, 1995.

Sunderkotter, C., et al., Macrophages And Angiogenesis, J. Leuk. Biol. 55:410–422, 1994.

Warren, RP, et al., Augmentation Of Natural Killer Activity By Imuvert: A Biological Response Modifier Derived From Serratia Marcescens. Molec. Biother. 1:145–151, 1989.

Williams, JH, Jr., et al., Ingibition Of Alveolar Macrophaces By Pentoxifylline Crit. Care Med. 19:1073–1078, 1991.

Wilson, CB, et al., Effects Of Muramyl Dipeptide On Superoxide Anion Release And On Anti–Microbial Activity Of Human Macrophagesl. Clin. Exp. Immunol. 49:371–376, 1982.

METHOD OF ATTENUATION OF NERVOUS SYSTEM DAMAGE

CROSS REFERENCE TO RELATED APPLICATION

This application is a continuation of application Ser. No. 08/227,533 filed Apr. 14, 1994, now U.S. Pat. No. 5,574,022.

BACKGROUND OF THE INVENTION

1. Field of the Invention

This invention relates to the attenuation of nervous system damage after injury produced externally or by processes occurring within the organism itself. More particularly, the invention relates to the prevention of sequelae of nervous system injury by the coadministration of steroid hormones or steroid precursors such as pregnenolone, pregnenolone sulfate, and structurally similar organic compounds together with substances such as bacterial lipopolysaccharides (hereinafter referred to by the abbreviation LPS), ImuVert, muramyl dipeptide, and pyran or dextran polymers that stimulate secretion of cytokines by glia, monocytes, macrophages, and Schwann cells and with non-steroidal antiinflammatory substances or drugs (hereinafter referred to by the abbreviation NSAIDs) such as aspirin, indomethacin, ibuprofen, acetaminophen, sodium salicylate, BW755c, diclofenac, naproxen, and BF389 that suppress the inflammatory effects of enhanced activation of the above-mentioned non-neural cells while not diminishing the recovery-promoting effects of the cytokines secreted by them.

2. Description of the Prior Art

Externally initiated injuries to the nervous system are exemplified by contusions or compressions produced by direct blows to the head or spinal cord or by injuries to brain or spinal cord as a result of falls or other accidents; by penetrating wounds caused by knife blades, bullets, or other types of foreign objects or by complete severance of the spinal cord caused by such wounds; by X-rays, electromagnetic radiation, or exposure to radioactive fallout; by infections caused by bacteria, protozoa, yeast, fungi, or viruses. Indigenous modes of injury are exemplified by partial or complete occlusions of blood vessels by immune complexes, platelet aggregations, arteriosclerotic plaques, or sickle cell erythrocytes; by aneurysms, strokes, vascular spasms; by deposition of lipofuscin and/or amyloid; by autoimmune processes in allergic reactions, lupus erythematosus, and demyelinating disorders; by variously produced irritative inflammatory processes in endothelial cells of capillaries of blood vessels which result in permeabilization of blood vessels and the consequent edematous swelling in regions of the brain and spinal cord; or by invasive lesions caused by benign or malignant tumors.

Both regionally and globally, the whole functional terrain in the nervous system is disturbed after injury occurs. There is damage to microvasculature and there are losses of neuronal cells, decreases in neuronal processes in surviving cells, and increases in various glial elements and/or changes in their proportions and functions. Accelerated degeneration of neural, endothelial, neuroendocrine, and endocrine elements together with incoordination of the networks of relations among the cellular components of the immune system with coincident disruption of neurovascular relations and breakdown of the blood-brain barrier in the affected regions predispose to development of circulating and cellular autoantibodies to various polymeric cellular components of cellular and extracellular components in the disrupted regions. This leads to enhanced cellular destruction and deposition of the relatively indigestible debris of immune complexes in capillaries and extracellular sites. A further consequence of perturbation of the immune system is immunosuppression, with resultant activation of latent viruses destructive to the nervous system.

In view of the great complexity of the biological situations touched upon above and the ripple-like, radiating effects of injury, it is not surprising that there are changes in a myriad of measured parameters. A primary therapeutic task has been to identify key therapeutically-accessible, rate-limiting processes and to facilitate their relief. The remarkable self-organizing properties of biological systems often enable them to begin to function adaptively once effective communications among their relevant subunits are reinstituted.

Injuries to the nervous system have been treated in the past using supportive and surgical procedures. For example, many injuries have been treated simply by immobilizing the head and neck for a period of time. The recent advances in nursing and acute medical and rehabilitational care are largely responsible for the improved longevity of patients with spinal-cord injuries, but there have not been accompanying improvements in neurologic outcome. Only recently have advances been made that show medication can enhance recovery from nervous system damage. Specifically, Bracken et al. in *The New England Journal of Medicine*, 322:1405-1412 (May 17, 1990), reported that in patients with acute spinal-cord injury, treatment with methylprednisolone can improve neurologic recovery when the medication is given within the first eight hours after injury, however, treatment with naloxone does not improve neurologic recovery. The Bracken et al. study shows that methylprednisolone had no effect at low doses and was only effective at high, receptor saturating levels.

SUMMARY OF THE INVENTION

It is an object of this invention to provide a method and compositions for attenuating progression of damage to the nervous system once injury has occurred.

It is another object of this invention to provide a combination drug treatment for attenuating nervous system damage such as may occur with spinal cord injuries and the like.

According to the invention, a treatment has been developed for attenuation of nervous system damage after injury wherever in the nervous system it occurs and by whatever means it is produced. It consists of coadministration soon after injury of steroid hormones or steroid hormone precursors such as PREG, PREG-S, or PREG esters that readily give rise to PREG and/or PREG-S, together with one of several substances that stimulate secretion of cytokines by glia, monocytes, macrophages, and Schwann cells and with a NSAID to suppress inflammatory effects of enhanced activation of the above-mentioned non-neural cells while not diminishing the recovery promoting effects of the cytokines secreted by them. Similarities in nervous system function in various mammals, including human beings, as well as much previous experience in the field, indicate that such treatment will be effective in attenuation of nervous system damage in men as well as in rats.

Although cytokine secretory stimulants and antiinflammatory substances, alone and together, show modest degrees of attenuation of nervous system damage, never before have such substances been proposed to be used in conjunction with steroid hormones or steroid hormone precursors such as PREG or PREG-S for this purpose. The combination of the three compounds produces remarkably superior results.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

Research on spinal cord injury largely has focused on glial proliferation and scarring, neuronal sprouting and regeneration, and the phagocytic activity of macrophages. Macrophages synthesize and secrete a variety of macromolecules that contribute to the healing of wounds (1). Some of the secretory products, such as tumor necrosis factor (2), prostaglandins (3), and oxygen free radicals (4) cause necrosis of foreign or invading cells; others aid wound healing by stimulating mitosis (5), angiogenesis (6) and reactive gliosis (7, 8). Other cytokines, such as the interleukins, coordinate immune responses (9). Microglia and astrocytes also show comparable secretory activity (10–12) in response to macrophage-released cytokines (7–10) or when stimulated directly by LPS (10–12).

Often conditions in injured nervous tissue are not sufficiently stimulatory, by themselves, to cause non-neural cells such as mentioned above to express fully their secretory capabilities. They must be activated by specific exogenously supplied agents. After having been primed by exposure to lymphokines released by lymphocytes, neutrophils or other cells at the site of inflammation, the macrophages must be made fully competent for secretion of cytokines by exposure to LPS or other activating molecules (13). Microglia and astrocytes must be activated similarly in order to fully express their secretory capabilities (10, 11).

However, the consequences of full secretory activation of the above cell types often cannot be adequately controlled by the organism without external intervention, and the macrophages often are aroused to a feeding frenzy following over-secretion of excess cytotoxic factors, resulting in cystic degeneration and cavitation and consequentially irreversible damage. The key to attenuation of injury to the nervous tissue and possibly to successful neural regeneration lies in adjusting the relationships between the injured tissue and overzealous non-neural defenders (14, 15).

In order to achieve attenuation of damage as a result of injury, it is necessary to facilitate adaptive coupling among relevant cellular components. The various steroids that abound in tissues and tissue fluids play key multifactorial roles in facilitating such coupling. Although mechanisms of effects in particular instances largely have not yet been defined at the molecular level, the overall experimental results and clinical observations suggest the roles of steroids to be those of pleiotropic facilitators of coordinative processes that enable immune, neural, and metabolic systems, separately and together, to cycle freely through their operational modes in achieving rebalancing when malfunctioning occurs (16).

Non-genomic and genomic effects are exerted by the non-covalent association of steroids with sites on macromolecular entities, affecting their conformations and, therefore, their functional states. Individual substances to which steroids bind may have several potential binding sites with varying affinities for different steroids. At the genomic level, there is extensive overlap in binding site competition among substances that bind to various steroid receptors as well as promiscuity in binding of different steroid-receptor complexes to the same DNA sequence. Modulation of some genes by steroids may involve combinatorial interactions. A continuum of binding specificities may exist from virtually complete promiscuity, such as is found in induction of the mammary tumor virus, to the extreme exclusivity of the induction of some secondary sex characteristics. High degree of binding specificity of a particular steroid-receptor complex to a DNA region near a particular gene, the transcription of which it regulates in target tissues, might be conferred by the nearby binding of other transcriptional regulatory proteins, including other steroid-receptor complexes (17–23).

This invention focuses on one steroid, pregnenolone (hereinafter referred to by the abbreviation PREG), in the context of the above formulation, with full awareness that the roles that may be ascribed to PREG are played out in environments in which many steroids coexist; and that at any time it is the pattern of distribution of these substances that helps determine regional functional states and behavior of the organism as a whole and not just the level of one particular steroid. This invention particularly includes the use of esters of PREG and PREG-S in which the 3β hydroxyl group is esterified to give a variety of esters that can be hydrolyzed in the gastrointestinal tract or absorbed as such and hydrolyzed to PREG or PREG-S in various tissues, including the brain and spinal cord. Such esters have the structure $R_1COOR_2$, formed from the acids $R_1COOH$ and the alcohols $HOR_2$, where the latter is PREG or PREG-S. $R_1$ is an alkyl, aryl, heterocyclic, or amino group or an H atom.

Figure 1:
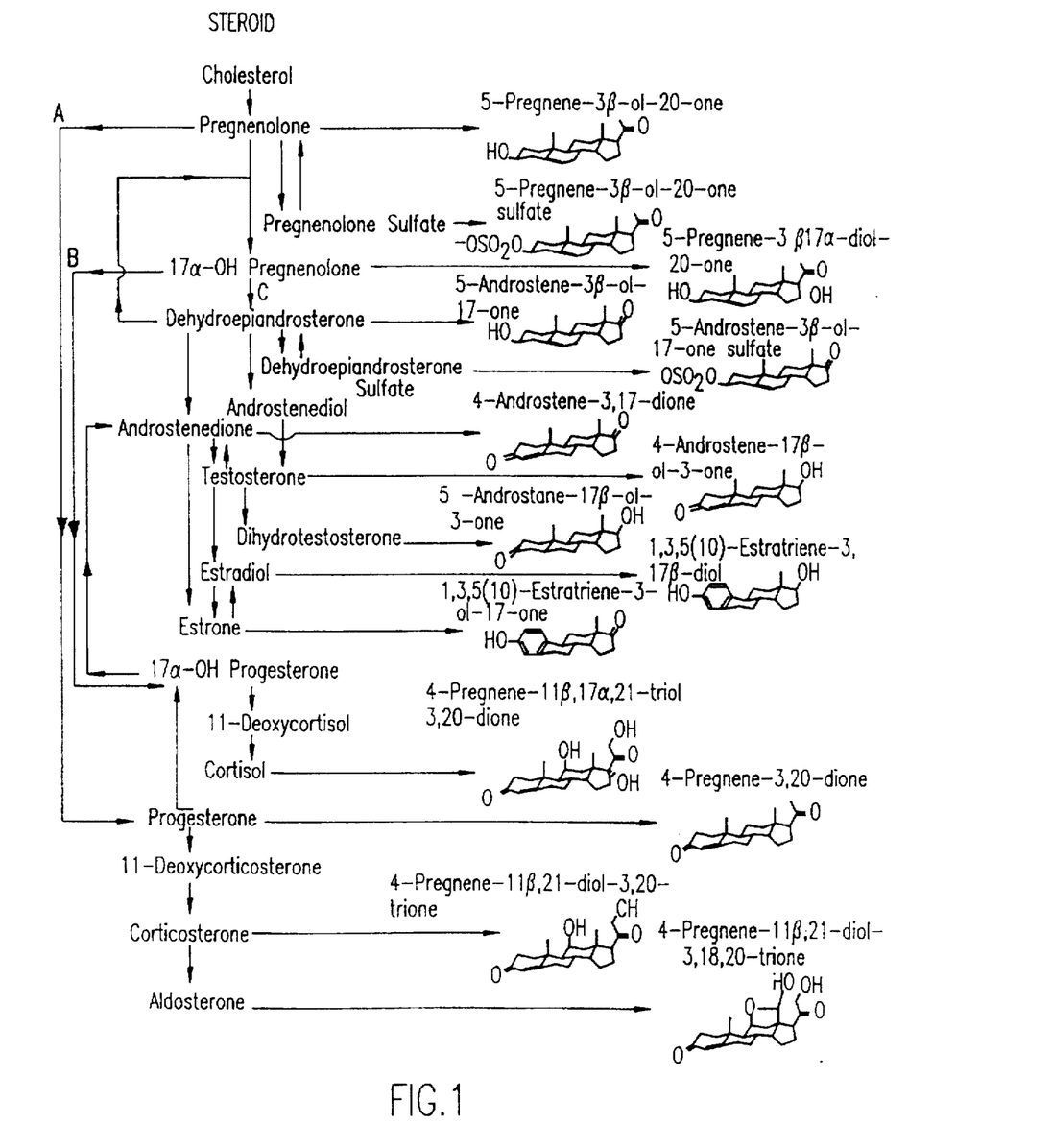
FIG. 1 is a skeletal outline of steroid metabolism.

FIG. 1 shows a skeletal outline of the steroid metabolic scheme as it may occur in the human organism as a whole. If one were to homogenize the entire organism and extract the homogenate appropriately, one could expect there to be the substances shown in FIG. 1 and many others derived from them, known and still unknown, and to be able to demonstrate the activities of enzymes that catalyze the required interconversions. However, it is highly unlikely that any single tissue or tissue fluid contains all of the substances and/or enzymes; and among those tissues in which they do exist, marked differences in levels would be found. All cells in the body probably require for regulation of their functions some or all of these steroids, whose combined activities range from modulation of membrane excitability to regulation of genomic transcription.

The biosynthesis of steroid hormones begins with cholesterol, from which the sex steroids, glucocorticoids, and mineralocorticoids all derive. PREG is the major precursor for the steroid hormones. It is formed from cholesterol in mitochondria of tissues that produce steroid hormones. The rate of steroid synthesis is controlled by the delivery of cholesterol from cytoplasmic inclusion droplets to the inner mitochondrial membrane, where steroidogenesis begins by production of PREG from cholesterol by action of cytochrome P-450scc (side-chain cleavage enzyme), a reaction found in peripheral tissues as well as in brain. Formation of PREG is regulated by pituitary hormones, such as luteinizing hormone and follicle-stimulating hormone in ovaries and testes, ACTH and one or more non-ACTH pituitary peptides in adrenals, and possibly hypothalamic hormones at the latter and other sites. PREG can go directly to progesterone and thence to aldosterone (route A, FIG. 1) or to 17α-OH PREG, which is a precursor for cortisol formation (route B, FIG. 1) and for sex-related steroids (route C, FIG. 1). Route A can contribute to route B and route B to route C, as shown. Dehydroepiandrosterone, the first product in route C, can inhibit the flow through routes B and C by inhibiting conversion of PREG to 17α-OH PREG. PREG is of major interest because it lies at the branchpoint at which decisions are made as to how the subsequent metabolic flow is fractionated between the mineralocorticoid, androgen→estrogen, and glucocorticoid pathways. Further discussion of steroid metabolism is eschewed since reviews, books, and symposia on all aspects of the subject abound (see ref 24–31 and literature citations therein).

Since PREG is the precursor of all of the known steroid hormones, it is not surprising that under special experimental circumstances it exhibits effects of every hormone formed from it. It also has its own relatively specific effects, e.g. on $GABA_A$ and NMDA receptors (32–39) and serves as precursor for the formation of a panoply of different steroids and steroid derivatives. PREG, the parent steroid, also can play synergic roles with other steroids at genomic and non-genomic sites, facilitating their actions in helper-like fashion through allosteric effects exerted by binding at different loci to the same entities. An adequate supply of locally synthesized and/or externally supplied PREG could ensure near-optimal modulation of non-genomic and genomic processes at sites at which enzyme activities exist for the subsequent conversion of PREG to tissue-specific patterns of steroids.

With aging, continued stress, injury or disease, decreases in amounts or incoordination in rates of formation of PREG and steroids arising from it can occur globally throughout the organism or locally at specific tissue sites, which may lead to failure of maintenance of optimal steroid patterns and, therefore, to decreased capacity to respond adaptively to demands of injury (40). In normal individuals mean blood serum levels of PREG and PREG sulfate (herein referred to by the abbreviation PREG-S) decrease with age, those of PREG-S showing a 60% reduction at a mean age of 75 yr by comparison with the values observed at a mean age of 35 yr (unpublished results).

Levels of PREG many times higher than in plasma are found in human brain and in cranial and peripheral nerves (41, 42), at which sites PREG is present in oligodendrocytes and Schwann cells, respectively, and in which cells it is formed independently of the peripheral endocrine system and from which it can be released during nerve activity. Cholesterol that is used for PREG synthesis may come either from preformed cholesterol delivered to sites of synthesis of PREG or may be furnished by indigenous synthesis of cholesterol from acetyl coenzyme A (43–49). Ordinarily, facile alterations can be made in rates of flow of cholesterol to sites of PREG synthesis through adjustments in rates of transport and biosynthetic pathways so that an adequate supply of precursor is maintained. However, upon injury, either one or both sources of precursor supply may become rate-limiting, and the ability to form and release PREG and substances formed from it could become compromised. If both lines of supply of cholesterol were constricted, inability or decreased ability to synthesize PREG and its derivatives in nerve tissue and to release them at a sufficiently rapid rate could seriously handicap the many functions they regulate or modulate, and adverse effects would occur, limiting extent of self-repair at all stages after injury occurs. Administration of PREG would prevent such undesirable effects from occurring.

Restoration of normal steroid patterns by administration of PREG alone or together with much smaller than currently employed amounts of other steroids is less physiologically disturbing than is administration of arbitrarily selected amounts of more potent substances that derive from it, e.g., cortisone, sex steroids, or aldosterone, because myriad feedback inhibitory loci exist in steroid formation beginning with the synthesis of PREG from cholesterol, which in different tissues may be under control of different pituitary hormones, and because there exists widespread competition of steroids for binding to receptor and allosteric sites. For example, administration of large amounts of dehydroepiandrosterone (DHEA), the first substance in route C (FIG. 1), retards metabolite flow through routes B and C by inhibiting conversion of PREG to 17α-OH PREG, upsetting the balances of steroid hormones in various tissues and, therefore, tending to decrease adaptability. Nonetheless, experimental results discussed below with DHEA-S, the sulfate derivative of DHEA, demonstrate that steroid hormones will be of some utility in the practice of the invention.

Thus, PREG helps maintain a balanced steroidal environment, minimizing disturbances in allosteric and transcriptional relationships that large excesses of administration of particular steroids might bring about by competing with other steroids. In those instances in which desired therapeutic goals cannot be attained without actual administration of particular specialized steroids, themselves, co-administration of PREG with relatively small amounts of such steroids might give the same physiological effects as would administration of larger amounts of the latter alone. This would also explain why slight improvement in function after spinal cord injury could be obtained only with superhigh doses of methylprednisolone (Bracken et al., ibid.). This would minimize risk of feedback inhibition of formation and/or release of pituitary factors that play a role in steroid hormone synthesis and thus attenuate the consequent homeostatic disturbance that would occur upon cessation of administration of steroid or a reduction in dosage.

Importantly, no toxic effects were observed in experimental animals following large doses of PREG by oral, subcutaneous, or intraperitoneal routes (51). PREG also was found to be without observable toxicity in man when given parentally or orally in a number of older studies (e.g. see ref. 52–61). The lack of toxicity in man has been confirmed in a current study with Alzheimer patients on daily oral intake of 525 mg for 3 months; and orally administered PREG has been shown to be readily absorbed (in preparation). That even low oral doses of PREG can exert CNS effects in man was shown in a study in which 1 mg of PREG given orally before sleep to male volunteers significantly increased the amount of time spent in slow wave sleep and depressed EEG sigma (62).

The use of the naturally-occurring non-toxic PREG therapeutically, alone or together with other substances as suggested in the foregoing, is most advantageous and its efficacy documented experimentally in the following pages. The metabolic machinery for managing its disposition is in place at various tissue sites. Its administration in appropriate amounts in situations in which its availability is insufficient for normal function to take place does not create serious problems of physiological reorganization.

We have chosen controlled injury to the rat spinal cord as the paradigm by which to represent central nervous system injury in general, and to develop agents that significantly reduce adverse histopathological changes, enhance axonal regeneration and improve functional recovery. Similarity in nervous system function in various mammals, including human beings, as well as much previous experience in the field indicate that such therapeutic agents also will be damage-attenuators and repair-enhancers in human beings as well as in rats.

Materials and Methods

Test Animals and Surgical Procedures. Random-bred Sprague-Dawley female rats (170–200 grams) were anesthetized with 4% chloral hydrate (400 mg/kg, intraperitoneally), shaved, and the dorsal skin scrubbed with benzalkonium chloride (0.13% aqueous). Using aseptic surgical technique, a laminectomy was performed at T8, while taking care to leave the dura intact. A #5 Dumont jewelers forceps then was introduced between the dura mater and the bone, and the spinal cord was compressed for two seconds. Hemostasis was secured by topical application of Avitene (Med Chem Products, Inc., Woburn, Mass. 01801). Drug or control pellets were implanted subcutaneously into a pocket prepared by lateral extension of the rostral margin of the incision or into a second incision made just lateral to the rostral margin of the first one. Care was taken to eliminate any accumulation of tissue fluid prior to implanting the pellets. If more than one pellet was implanted, separate sites were chosen for each. The wounds were closed by suturing the underlying muscle with 6-0 silk and the skin incisions with wound clips. Each animal was housed individually and urine expressed by manual compression of the abdomen twice daily until bladder control was restored (7–10 days).

Substances Tested. All pellets were obtained from Innovative Research of America (Toledo, Ohio 43606) and contained matrix alone for controls, 50 mg of PREG, or 25 mg of acetylsalicylic acid (hereinafter referred to by the abbreviation ASP). The matrix provided continual release of the drug for 21 days (i.e., 2.38 mg PREG or 1.19 mg ASP per day). The pellets were disc-shaped and were approximately 6 mm in diameter and 2 mm thick. Rats receiving LPS were given daily intraperitoneal injections of 0.2 mg LPS from *Salmonella enteritidis* (Sigma) in 0.1 ml sterile, pyrogen-free water. Those receiving indomethacin (hereinafter referred to by the abbreviation IM) were given daily intraperitoneal injections of 0.2 mg IM sodium trihydrate (Indocin. iv., Merck Sharp & Dohme).

Histological Procedures. On the 21st experimental postoperative day, the rats were anesthetized and euthanized by intracardial perfusion with 15 ml saline followed by 250 ml of Bouin's fixative. The vertebral column was removed immediately and immersed for 24 hours in fixative and 48 hours in 70% ethanol. The spinal cord then was dissected from the vertebral column, dehydrated, and embedded in Paraplast (Fisher Scientific Co., Pittsburgh, Pa.). Serial longitudinal sections were cut at 10 pm thickness in either the horizontal or vertical plane. Every tenth slide was stained with H&E for examination of cellular detail and for image analysis, and adjacent slides were impregnated with protargol for visualization of nerve fibers.

Image analysis was performed with appropriate illumination and background correction using the BioQuant system (BQ Meg IV, Biometrics Inc.). Only those sections containing a portion of central canal in proximity to the lesion were studied, in order to ensure that observations were made at the same level in all samples. The selected slides were then coded and randomized. A 4X objective was used so that the entire lesion could be included in one microscope field. The area of the lesion was estimated by drawing a line around the entire lesion and measuring the area within the perimeter. The area of the cavities within the lesion was determined by using a threshold setting that allowed measurement of areas devoid of cells. The number of cells within the lesion was obtained by using a threshold setting that counted only the cell nuclei within the lesion. This value was divided by the area of the lesion to obtain the number of cells per $mm^2$ of lesion.

Functional Assessment. The walking ability of all operated rats was evaluated daily in double-blind fashion independently by two investigators.

Evaluations were made without knowledge of the treatment group or of the previous day's ratings. The rating system used was the modification of the Tarlov scale recommended by Wrathall et al. (63): 0, complete hindlimb paralysis; 1, barely perceptible hindlimb movements; 2, clearcut hindlimb movements which do not result in weight bearing or locomotion; 3, hindlimbs are used to crawl but do not support the weight of the body; 4, hindlimbs are used for support of the body and walking but with clearcut disability; 5, posture and walking ability is nearly normal.

Statistical Analysis. The locomotor function was analyzed statistically by the analysis of variance (ANOVA) with multiple comparisons made by the Student-Newman-Keuls procedure. The scale of 1–5 consists of an ordered metric level of measurement where the relative ordering of the intercategory distances is known even though their absolute magnitude cannot be measured (64). Such data can be treated as though it had been measured at equal intervals, and the ANOVA is an appropriate and sensitive method of statistical analysis of such data (64). Nonparametric ANOVA (Dunn's procedure) was performed in those instances when the parametric procedure was inappropriate (e.g., when the Bartlett test revealed statistically significant differences in the variance between the treatment groups).

RESULTS

Figure 2A:
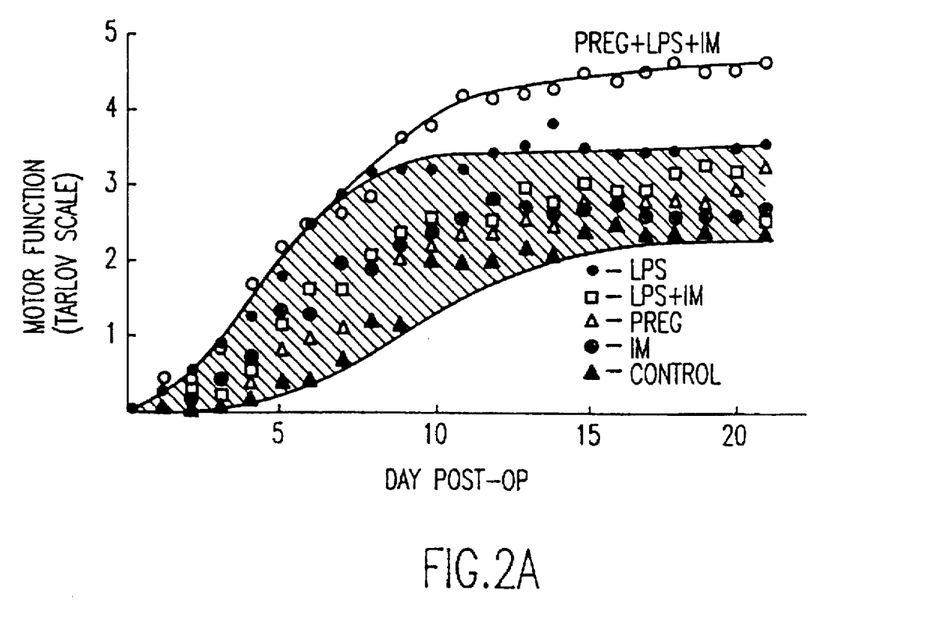
FIGS. 2a and 2b are line graphs illustrating motor function in rats receiving different treatments as a function of time after spinal cord compression.

In the first set of experiments (Table 1, FIG. 2A), a group of rats implanted with control pellets immediately after injury was compared with 5 other groups treated with IM, LPS, or PREG alone or with LPS+IM or PREG+LPS+IM, as described under Methods. The only experimental group showing statistically significant attenuation of decrement in motor function by comparison with the controls was that receiving PREG+LPS+IM (Table 1; FIG. 2A). The results were remarkable in that 4 of 6 animals in the PREG+LPS+IM group walked almost normally at 21 days (Table 1) and the mean daily Tarlov scores were higher than those of all of the other groups between the 7th and 21st postoperative days, although all treatment groups improved in walking ability to some extent (FIG. 2A). Such a result as that with PREG+LPS+IM group has not been observed by us in the many years we have employed the same experimental paradigm for study of the therapeutic potential of various test substances.

Table 1 shows the total area occupied by the lesion was significantly smaller in the PREG+LPS+IM group than in the controls, while the other experimental groups did not show a statistically significant difference from the controls.

TABLE 1

Motor function and histological evaluation of spinal cord damage in rats after standardized crush at T6

| Group | | No. of rats† | Tarlov scale rating | | | | Area of lesion (mm)² | | Area of cavity Area of lesion | |
|---|---|---|---|---|---|---|---|---|---|---|
| | | | 10 days | | 21 days | | | | | |
| No. | Treatment* | | Mean | S.E.M. | Mean | S.E.M. | Mean | S.E.M. | Mean | S.E.M. |
| 1 | Control | 6 | 2.00 | 0.29 | 2.25 | 0.36 | 1.62 | 0.11 | 0.577 | 0.050 |
| 2 | Indomethacin (IM) | 6 | 2.33 | 0.38 | 2.25 | 0.36 | 1.63 | 0.14 | 0.641 | 0.049 |
| 3 | Lipopolysaccharide (LPS) | 4 | 3.12 | 0.52 | 3.50 | 0.61 | 1.64 | 0.08 | 0.382§ | 0.048 |
| 4 | Pregnenolone (PREG) | 6 | 2.17 | 0.40 | 3.25 | 0.36 | 1.84 | 0.13 | 0.546 | 0.047 |
| 5 | LPS + IM | 4 | 2.50 | 0.35 | 3.20 | 0.30 | 1.63 | 0.14 | 0.297‡ | 0.052 |
| 6 | PREG + LPS + IM | 6 | 4.08‡ | 0.36 | 4.50‡ | 0.34 | 1.14¶ | 0.09 | 0.246‡ | 0.037 |

*Groups 1, 2, 3, and 5 were implanted with 21-day release placebo pellets and groups 4 and 6 with the same size pellets containing 50 mg PREG
†Data is recorded only for animals surviving the experimental period of 21 days. S.E.M., standard error of mean.
‡P value for comparison with controls is <0.01
§P value for comparison with controls is <0.05
¶P value for comparison with controls is <0.01

The proportions of the areas of the lesions occupied by cavities were least in the case of the PREG+LPS+IM group. The mean ratios of cavity to lesion also were significantly smaller in the LPS and LSP+IM groups than in the controls. The fact that the cavitation ratios were not significantly reduced in the case of the groups receiving IM or PREG alone is consistent with the interpretation that stimulation of release and exchange of cytokines, as by LPS, is a requirement for the attenuation of damage resulting from the injury. In some instances, the combination of LPS+IM gives a somewhat better histological result than LPS alone. This is consistent with the idea that a decrease in inflammatory processes, such as results from administration of IM, is important in attenuating subsequent damage. The remarkable additional attenuative effect observed when PREG is present in the therapeutic regimen is attributable to its pleiotropic effects, among which are effects on gene transcription (17-23), maintenance of neuronal excitability (32-39), antiinflammatory action (52-61), and formation of other steroidal substances from it, as shown in FIG. 1, that exert specific hormonal effects.

Figure 2B:
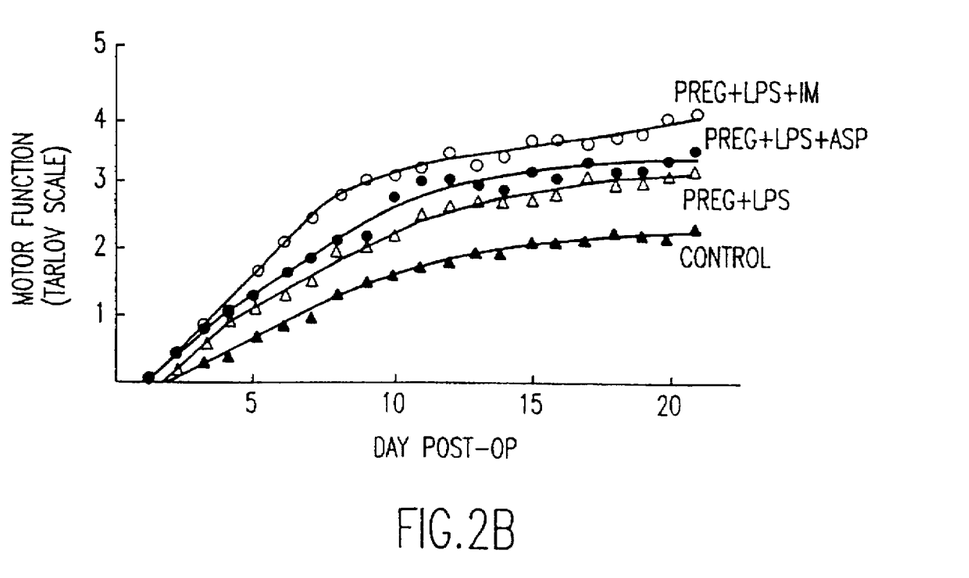
Figure 3A:
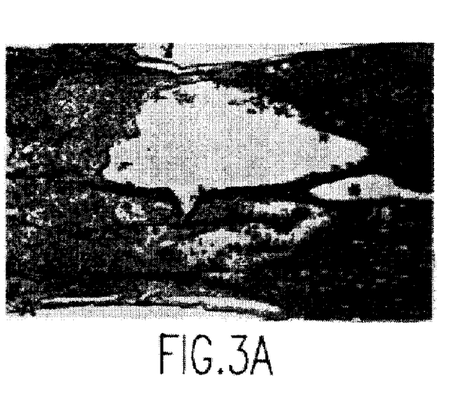
FIG. 3 are histological results showing the injury attenuating effects of PREG+LPS+IM.
Figure 3B:
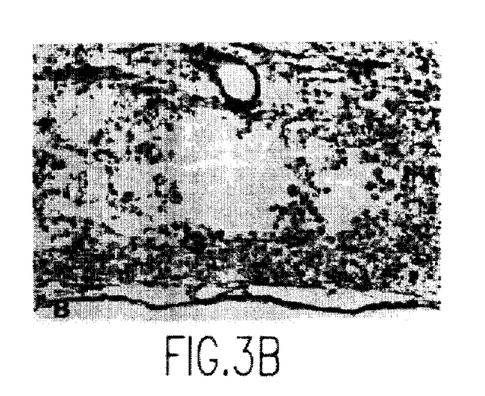
Figure 3C:
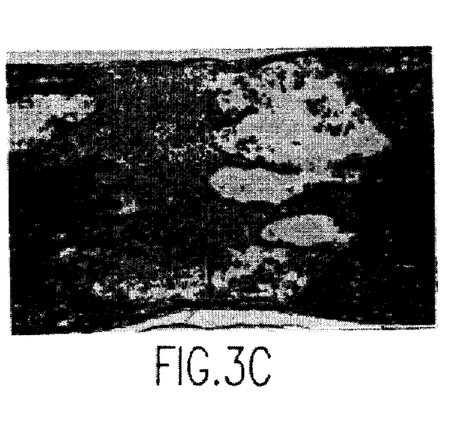
Figure 3D:
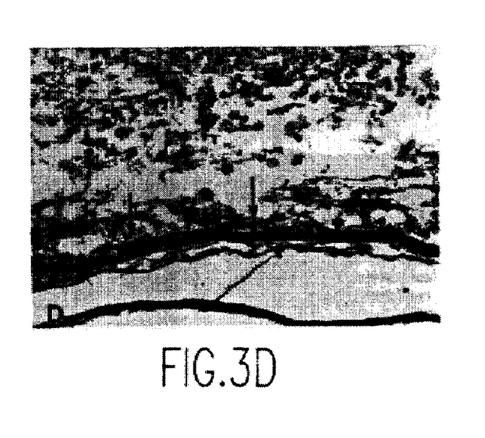
Figure 3E:
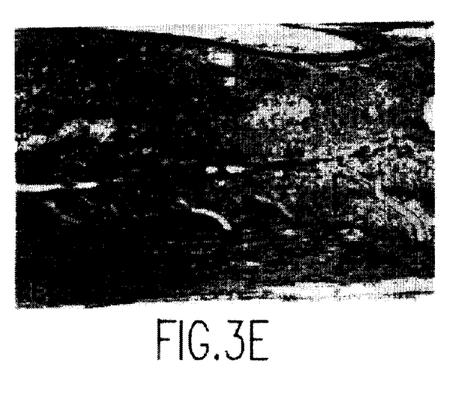
Figure 3F:
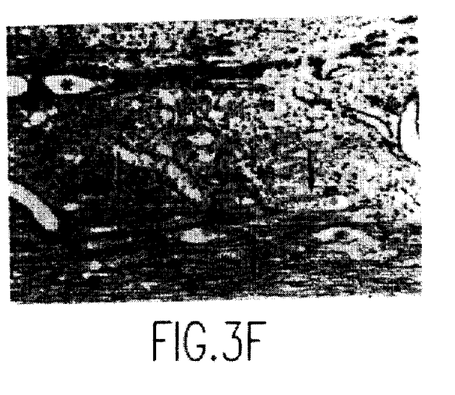
Figure 3G:
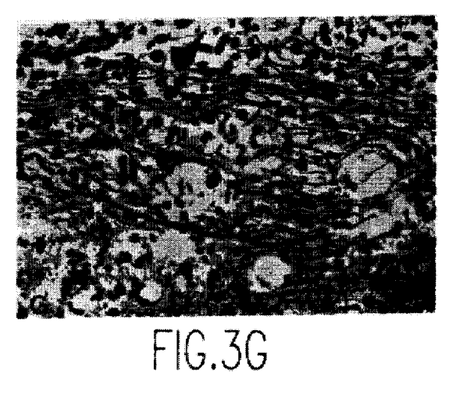
Figure 3H:
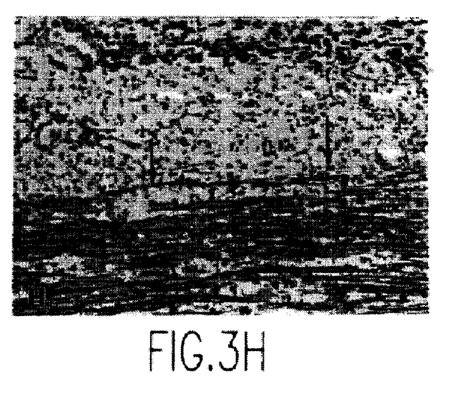

A second experiment (Table 2; FIG. 2B) was performed with 4 groups of rats: control, PREG+LPS, PREG+LPS+IM, and PREG+LPS+ASP. In the latter group ASP replaced IM as an antiinflammatory agent. In each of the above three experimental groups there was a decrement in damage to motor function by comparison with controls at all times through the 21st postoperative day, which was calculated to be statistically significant at days 10 and 21.

TABLE 2

Motor function and histological evaluation of spinal cord damage in rats after standardized crush at T8
(Note: Longitudinal sections cut vertically so that the spared tissue located ventrally could be measured)

| Group | | No. of rate | Tarlov scale rating | | | | Area of lesion (sq. mm.) | | Area of cavity/ Area of Lesion | | Cells/sq. mm. of Lesion | | *Histological Sparing (μM) | |
|---|---|---|---|---|---|---|---|---|---|---|---|---|---|---|
| | | | 10 days | | 21 days | | | | | | | | | |
| No. | Treatment | | Mean | S.E.M. | Mean | S.E.M. | Mean | S.E.M. | Mean | S.E.M. | Mean | S.E.M. | Mean | S.E.M. |
| 1 | Control | 9 | 1.67 | 0.093 | 2.39 | 0.103 | 1.89 | 0.122 | 0.526 | 0.038 | 14,739 | 1,160 | 58 | 15.4 |
| 2 | PREG ‡ LPS | 10 | 2.22§ | 0.120 | 3.15‡ | 0.198 | 1.77 | 0.137 | 0.517 | 0.046 | 14,599 | 1,058 | 131 | 33.1 |
| 3 | PREG ‡ LPS ‡ IM | 9 | 3.12¶ | 0.269 | 4.12¶ | 0.259 | 1.33* | 0.144 | 0.357‡ | 0.040 | 21,408‡ | 1,660 | 724¶ | 204.0 |
| 4 | PREG ‡ LPS ‡ ASP | 9 | 2.80§ | 0.193 | 3.52¶ | 0.160 | 1.63 | 0.087 | 0.445 | 0.038 | 16,719 | 916 | 214 | 71.9 |

*Variances were not homogeneous. ANOVA therefore performed after log transformation of data.
‡P value for comparison with controls is <0.01
§P value for comparison with controls is <0.05
¶P value for comparison with controls is <0.001

The remarkable effect of PREG is illustrated by the fact that 6 of 10 animals of the PREG+LPS+IM group were able to walk in almost normal fashion at the end of the experiment. One of the 10 rats in the PREG+LPS+ASP group also could walk almost normally but none of the animals in the PREG+LPS or control groups could walk. The relative degrees of cavitation of the lesion area and the cellularity of the lesion were significantly decreased and increased, respectively, only in the PREG+LPS+IM group, although the respective mean values for the PREG+LPS+ASP group also were in the same direction. The somewhat lesser attenuative effect observed in the latter group may be related to the relatively low dose of ASP used.

The results at the cellular tissue level obtained with the PREG+LPS+IM combination are illustrated in FIG. 3 and described in the legend to the individual panels in FIG. 3. To our knowledge, no previously proposed treatment for attenuation of nervous system damage has given an effect comparable to that which has been observed with PREG+LPS+IM. There were remarkable histological differences between the controls (FIG. 3 panels A and B) and the PREG+LPS+IM group (FIG. 3 panels E and F).

LEGEND FOR FIG. 3

FIG. 3. Midsagittal sections of spinal cord through site of lesion; 21 days postoperative. In each photomicrograph, the dorsal part of cord is at the top and the ventral part is at the bottom. A. Vehicle treatment (control); H&E, X40. In the center of the lesion, a large cavity occupies the dorsal part of the cord and smaller areas of cavitation are seen ventrally. The central canal, seen in the undamaged tissue at the right side of the photograph, shows a characteristic dilatation (*) near the lesion. B. Vehicle-treatment (control); H&E, X100. Higher magnification shows the lesion site to be heavily infiltrated by large macrophages. C. PREG+LPS treatment; H&E, X40. Cavitation is most notable at the margins of the lesion bordering the dark-staining intact spinal tissue. The largest cavities are dorsal to the level of the central canal, which is indicated by an asterisk (*), while smaller areas of cavitation are seen ventrally. There is a thin rim of residual spinal tissue at the ventral margin of the lesion (arrow). D. PREG+LPS treatment; H&E, X100. Higher magnification reveals a loose arrangement of macrophages at the ventral region of the lesion and the cellularity of the spared ventral tissue (arrows) lying subjacent to the pia-arachnoid, subdural space and dura mater. E. PREG+LPS+IM treatment; H&E, X36. In this photograph, the lesion is to the right and the undamaged cord to the left. The dorsal region of the lesion contains less cavitation and is more densely cellular than in the animals treated with vehicle or PREG+LPS (compare with panels A and C). The tissue ventral to the central canal (*) is characterized by sparing of the white matter (arrow) and ingrowth of blood vessels (arrowheads). From the central canal emerges a stream of cells that enter the lesion. F. PREG+LPS+IM treatment; H&E, X90. This higher magnification photograph of a portion of panel E illustrates that the cells migrating into the lesion from the central canal (*) are ependymal cells. The staining properties of the spared ventral white matter (arrows) is consistent with that of myelinated nerve fibers. The blood vessels entering the ventral gray matter include large capillaries (left arrowhead) and arterioles (right arrowhead). G. PREG+LPS+IM treatment; Protargol, X180. A modest number of nerve fibers course within the lesion. These have the characteristics of regenerating axons. They vary from fine to medium in diameter, are varicose in appearance, and are oriented by the cellular environment. Note especially how they tend to avoid regions of cystic degeneration. H. PREG+LPS+IM treatment; Protargol, X90. This section, which is serial to that of panel F, shows that the spared tissue in the ventral white matter (arrows) consists of normal-appearing, longitudinally-oriented, nonvaricose nerve fibers. A small number of extremely fine nerve fibers are present in the lesion dorsal to the spared tissue.

Similar experiments conducted with dehydroepiandrosterone sulfate (DHEA-S) showed that significant reduction in lesion size can be achieved provided the steroid is administered in combination with LPS and IM. This effect was identical to that obtained with PREG+LPS+IM. However, treatment with DHEA-S+LPS+IM was significantly less effective in restoring locomotor function than was the treatment with PREG+LPS+IM. Taken together, these observations further support the hypotheses (a) that protocols involving combinations of therapeutic agents provide a more effective means of treating spinal cord injury than do treatments with single agents alone and (b) that the pharmacological actions of the recommended therapeutic agents are highly effective.

While the invention has been described in terms of its preferred embodiments, those skilled in the art will recognize that the invention can be practiced with modification within the spirit and scope of the appended claims.

REFERENCES

1. Hunt T K, Knighton D R, Thakral K K, Goodson W H and Andrews W S. Studies on inflammation and wound healing: angiogenesis and collagen synthesis stimulated in vivo by resident and activated wound macrophages. *Surgery* 96:48–54, 1984.
2. Satoh M, Oshima H, Abe S, Yamazaki M and Mizuno D. Role of in vivo scavenger function of macrophages in priming for endogenous production of tumor necrosis factor. *J Biol Response Mod* 6:499–511, 1987.
3. Snider M E, Fertel R H, and Zwilling B S. Production of arachidonic acid metabolites by operationally defined macrophage subsets. *Prostaglandins* 25:491–501, 1983.
4. Pabst M J, Cummings N P, Hedegaard H B and Johnston, Jr. R B. Human macrophages may normally be "primed" for a strong oxygen radical response. *Adv Exp Med Biol* 166:215–221, 1983.
5. Duff G W and Durum S K. The pyrogenic and mitogenic actions of interleukin-1 are related. *Nature* 30:449–451, 1983.
6. Koch A E, Polverini P J and Leibovich S J. Induction of neovascularization by activated human monocytes. *J Leukocyte Biol* 39:233–238, 1986.
7. Giulian D and Lachman L B. Interleukin-1 stimulation of astroglial proliferation after brain injury. *Science* 228:497–499, 1985.
8. Logan A, Frautschy S A, Gonzalez A M, Sporn M B and Baird A. Enhanced expression of transforming growth factor beta 1 in the rat brain after a localized cerebral injury. *Brain Res* 587:216–225, 1992.
9. Bahr, G M, Chedid L A and Behbehani K. Induction, in vitro and in vitro, of macrophage membrane interleukin-1 by adjuvant active synthetic muramyl peptides. *Cell Immunol* 107:443–454, 1987.
10. Lee S C, Liu W, Dickson D W, Brosnan C F and Berman J W. Cytokine production by human fetal microglia and astrocytes. Differential induction by LPS and IL-1 beta. *J Immunol* 150:2659–2667, 1993.
11. Lieberman A P, Pitha P M, Shin H S and Shin M L. Production of tumor necrosis factor and other cytokines by astrocytes stimulated with lipopolysaccharide or a neurotropic virus. *Proc Nat Acad Sci* 86:6348–6352, 1989.
12. Shari S F, Hariri R J, Chang V A, Barie P S, Wang R S and Ghajar J B. Human astrocyte production of tumour necrosis factor-alpha, interleukin-1 beta, and interleukin-6 following exposure to lipopolysaccharide endotoxin. *Neurol Res* 15:109–112, 1993.
13. Strassmann G, Springer T A, Haskill S J, Miraglia C C, Lanier L L and Adams D O. Antigens associated with the activation of murine mononuclear phagocytes in vivo: differential expression of lymphocyte function-associated antigen in the several stages of development. *Cell immunol* 94:265–275, 1985.
14. Roberts E. Living systems are tonically inhibited, autonomous optimizers, and disinhibition coupled to variability generation is their major organizing principle: inhibitory command-control at levels of membrane, genome, metabolism, brain, and society. *Neurochem Res* 16:409–421, 1991.
15. Roberts E. Dehydroepiandrosterone (DHEA) and its sulfate (DHEAS) as neural facilitators:
    effects on brain tissue in culture and on memory in young and old mice. A cyclic GMP hypothesis of action of DHEA and DHEAS in nervous system and other tissues. In: *The Biological Role of Dehydropeiandrosterone* (DHEA) (Eds. Kalimi M and Regelson W), pp. 13–40. Walter de Gruyter & Co., Berlin, 1990.

16. Flood J F, Morley J E and Roberts E, Memory-enhancing effects in male mice of pregnenolone and steroids metabolically derived from it. *Proc Natl Acad Sci USA* 89:1567–1571, 1992.

17. Jensen E V, Steroid hormone receptors. *Curr Top Pathol* 83:365–431, 1991.

18. Carson-Jurica M A, Schrader W T and O'Malley B W, Steroid receptor family: structure and functions. *Endocr Rev* 11:201–220, 1990.

19. Wahli W and Martinez E, Superfamily of steroid nuclear receptors: positive and negative regulators of gene expression. *FASEB J* 5:2243–2249, 1991.

20. Beato M, Transcriptional control by nuclear receptors. *FASEB J* 5:2044–2051, 1991.

21. Moore D D, Promiscuous behaviour in the steroid hormone receptor superfamily. *TINS* 12:165–168, 1989.

22. Evans R M, The steroid and thyroid hormone receptor superfamily. *Science* 240:889–895, 1988.

23. Schwabe J W R and Rhodes D, Beyond zinc fingers: steroid hormone receptors have a novel structural motif for DNA recognition. *TIBS* 16:291–296, 1991.

24. Burstein S and Gut M, Biosynthesis of pregnenolone. *Recent Prog Horm Res* 27:303–349, 1971.

25. Prasad V V K and Lieberman S, Reconsidering some of the biosynthetic pathways leading to formation of $C_{19}$-steroids. *Ann NY Acad Sci* 595:1–16, 1990.

26. Lieberman S, Greenfield N J and Wolfson A, A heuristic proposal for understanding steroidogenic processes. *Endocr Rev* 5:128–148, 1984.

27. Leszczynski D E and Schafer R M, Metabolic conversion of six steroid hormones by human plasma high-density lipoprotein. *Biochim Biophys Acta* 1083:18–28, 1991.

28. Provencher P H, Roy R and Belanger A, Pregnenolone fatty acid esters incorporated into lipoproteins: substrates in adrenal steroidogenesis. *Endocrinology* 130:2717–2724, 1992.

29. Mathur C, Prasad V V K, Raju V S, Welch M and Lieberman S, Steroids and their conjugates in the mammalian brain. *Proc Natl Acad Sci USA* 90:85–88, 1993.

30. Castagnetta L, d'Aquino S, Labrie F and Bradlow H L (eds.), Steroid Formation, Degradation, and Action in Peripheral Tissues. *Ann NY Acad Sci* 595:1–489, 1990.

31. Frairia R, Bradlow H L, and Gaidano G, Steroid-Protein Interactions: Basic and Clinical Aspects. *Ann NY Acad Sci* 538:1–326, 1988.

32. Majewska M D, Neurosteroids: endogenous bimodal modulators of the $GABA_A$ receptor. Mechanism of action and physiological significance. *Progr Neurobiol* 38:379–395, 1992.

33. Majewska M D, Mienville J-M and Vicini S, Neurosteroid pregnenolone sulfate antagonizes electrophysiological responses to GABA in neurons. *Neurosci Lett* 90:279–284, 1988.

34. Mienville J-M and Vicini S, Pregnenolone sulfate antagonizes $GABA_A$ receptor-mediated currents via a reduction of channel opening frequency. *Brain Res* 489:190–194, 1989.

35. Woodward R M, Polenzani L and Miledi R, Effects of steroids on γ-aminobutyric acid receptors expressed in Xenopus oocytes by poly(A)⁺ RNA from mammalian brain and retina. *Mol Pharm* 41:89–103, 1992.

36. Wu F-S, Gibbs T T and Farb D H, Pregnenolone sulfate: a positive allosteric modulator at the N-methyl-D-aspartate receptor. *Mol Pharm* 40:333–336, 1991.

37. Bowlby M R, Pregnenolone sulfate potentiation of N-methyl-D-aspartate receptor channels in hippocampal neurons. *Mol Pharm* 43:813–819, 1993.

38. Farb D H, Gibbs T T, Wu F-S, Gyenes M, Friedman L and Russek S J, Steroid modulation of amino acid neurotransmitter receptors. *Adv Biochem Psychopharmacol* 47:119–131, 1992.

39. Irwin R P, Maragakis N J, Rogawski M A, Purdy R H, Farb D H and Paul S M, Pregnenolone sulfate augments NMDA receptor mediated increases in intracellular $Ca^{2+}$ in cultured rat hippocampal neurons. *Neurosci Lett* 141:30–34, 1992.

40. Roberts E and Fitten L J, Serum steroid levels in two old men with Alzheimer's disease (AD) before, during, and after oral administration of dehydroepiandrosterone (DHEA).

Pregnenolone synthesis may become rate-limiting in aging. In: *The Biological Role of Dehydroepiandrosterone* (DHEA) (Eds., Kalimi M and Regelson W), pp. 43–63. Walter de Gruyter & Co., Berlin, 1990.

41. Lanthier A and Patwardhan V V, Sex steroids and 5-en-3β-hydroxysteroids in specific regions of the human brain and cranial nerves. *J Steroid Biochem* 25:445–449, 1986.

42. Morfin R, Young J, Corpechot C, Egestad B, Sjovall J and Baulieu E-E, Neurosteroids: pregnenolone in human sciatic nerves. *Proc Natl Acad Sci USA* 89:6790–6793, 1992.

43. Le Goascogne C, Robel P, Gouezou M, Sananes N, Baulieu E-E and Waterman M, Neurosteroids: cytochrome $P-45_{sec}$ in rat brain. *Science* 237:1212–1215, 1987.

44. Hu Z Y, Bourreau E, Jung-Testas I, Robel P and Baulieu E-E, Neurosteroids: oligodendrocyte mitochondria convert cholesterol to pregnenolone. *Proc Natl Acad Sci USA* 84:8215–8219, 1987.

45. Jung-Testas I, Hu Z Y, Baulieu E-E, and Robel P, Steroid synthesis in rat brain cell cultures. *J Steroid Biochem* 34:511–519, 1989.

46. Jung-Testas I, Hu Z Y, Baulieu E E and Robel P, Neurosteroids: biosynthesis of pregnenolone and progesterone in primary cultures of rat glial cells. *Endocrinology* 125:2083–2091, 1989.

47. Akwa Y, Young J, Kabbadj K, Sancho M J, Zucman D, Vourc'h C, Jung-Testas I, Hu Z Y, Le Goascogne C, Jo D H, Corpechot C, Simon P, Baulieu E E and Robel P, Neurosteroids: biosynthesis, metabolism and function of pregnenolone and dehydroepiandrosterone in the brain. *J Steroid Biochem Molec Biol* 40:71–81, 1991.

48. Akwa Y, Sananes N, Gouezou M, Robel P, Baulieu E-E and LeGoascogne C, Astrocytes and neurosteroids: metabolism of pregnenolone and dehydroepiandrosterone. Regulation by cell density. *J Cell Biol* 121:135–143, 1993.

49. Vourc'h C, Eychenne B, Jo D-H, Raulin J, Lapous D, Baulieu E-E and Robel P, $\Delta^5$-3β-hydroxysteroid acyl transferase activity in the rat brain. *Steroids* 57:210–215, 1992.

50. Roberts E, Pregnenolone—from Selye to Alzheimer and a model of the pregnenolone binding site on the $GABA_A$ recept. *Biochem Pharm*, in press, 1994.

51 Henderson E, Weinberg M and Wright W A, Pregnenolone. *J Clin Endocrin* 10:455–474, 1950.

52. Hoagland H, Adventures in biological engineering. *Science* 100:63–67, 1944.

53. Pincus G and Hoagland H, Effects of administered pregnenolone on fatiguing psychomotor performance. *J Aviat Med* 15:98–115, 1944.

54. Pincus G and Hoagland H. Effects on industrial production of the administration of Δ5 pregnenolone to factory workers. I. *Psychosom Med* 7:342–346, 1945.
55. Pincus G, Hoagland H, Wilson C H and Fay N J. Effects on industrial production of the administration of Δ5 pregnenolone to factory workers. II. *Psychosom Med* 7:347–352, 1945.
56. Ishmael W K, Hellbraum A, Kuhn J F and Duffy M. The effects of certain steroid compounds on various manifestations of rheumatoid arthritis. *J Okla State Med Assoc* 42:434–437, 1949.
57. Freeman H, Pincus G, Johnson C W, Bachrach S, McCabe G E and MacGilpin H. Therapeutic efficacy of Δ5 pregnenolone in rheumatoid arthritis. *JAMA* 142:1124–1128, 1950.
58. Freeman H, Pincus G, Bachrach S, Johnson C W, McCabe G E and MacGilpin, Jr H H. Oral steroid medication in rheumatoid arthritis. *J Clin Endocrin* 10:1523–1532, 1950.
59. Freeman H, Pincus G, Bachrach S, Johnson C W, McCabe G E, MacGilpin Jr, H H and Scanlon J G. Oral steroid medication in rheumatoid arthritis. In: *Symposium on Steroids in Experimental and Clinical Practice* (Ed. White A), pp. 181–198, Blakiston, N.Y., 1951.
60. Davison R, Koets P, Snow W G and Gabrielson L G. Effects of delta 5 pregnenolone in rheumatoid arthritis. *Arch Intern Med* 85:365–388, 1950.
61. McGavack T H, Chevalley J and Weissberg J. The use of $\Delta^5$-pregnenolone in various clinical disorders. *J Clin Endocrinol* 11:559–577, 1951.
62. Steiger A, Trachsel L, Guldner J, Hemmeter U, Rothe B, Rupprecht R, Vedder H and Holsboer F. Neurosteroid pregnenolone induces sleep-EEG changes in man compatible with inverse agonistic $GABA_A$-receptor modulation. *Brain Res* 615:267–274, 1993.
63. Wrathall J R, Pettegrew R K and Harvey F. Spinal cord contusion in the rat: production of graded, reproducible injury groups. *Exp Neurol* 88: 108–122, 1985.
64. Abelson and Tukey, 1967. Efficient conversion of non-parametric information into a metric system. Pages 407–417 in "Quantitative Analysis of Social Problems" (E. R. Rufte, ed.) Addison-Wesley, Reading, Mass.

We claim:

1. A method for attenuating physical damage to a spinal cord of a patient and promoting recovery of motor functions, wherein said patient has a trauma of the spinal cord which is less than severing and which is sufficient to cause loss of motor function, comprising the steps of:

first administering to said patient a therapeutically effective amount of pregnenolone or pregnenolone sulfate;

second administering to said patient together with said pregenenolone or pregnenolone sulfate provided by said first administering step therapeutically effective amounts of (I) a substance that stimulates secretion of cytokines by macrophages, and (II) a non-steroidal antiinflammatory drug, said pregnenolone or pregnenolone sulfate provided in said first administering step, said substance that stimulates secretion of cytokines provided in said second administering step, and said non-steroidal anti-inflammatory drug administered in said second administering step being sufficient to repair physical damage to said patient's spinal cord and restore motor functions to said patient.

2. The method of claim 1 further comprising the step of selecting said non-steroidal anti-inflammatory drug provided in said second administering step from the group consisting of aspirin, indomethacine ibuprofen, acetaminophen, sodium salicylate, diclofenac, and naproxen.

3. The method of claim 2 wherein said non-steroidal antiinflamatory drug is aspirin.

4. The method of claim 2 wherein said non-steroidal antiinflamatory drug is indomethacin.

5. The method of claim 2 wherein said non-steroidal antiinflamatory drug is naproxen.

6. The method of claim 1 wherein said second step of administering includes the step of injecting said non-steroidal antiinflammatory drug in said patient.

7. The method of claim 1 further comprising the step of selecting said substance that stimulates secretion of cytokines from the group consisting of lipopolysaccharides, ImuVert, muramyl dipeptides, pyran polymers, and dextran polymers.

8. The method of claim 1 wherein said second step of administering includes the step of injecting said substance that stimulates secretion of cytokines in said patient.

* * * * *